(12) United States Patent
Kazakevich et al.

(10) Patent No.: US 9,204,787 B2
(45) Date of Patent: Dec. 8, 2015

(54) 360 DEGREE PANNING STEREO ENDOSCOPE

(71) Applicant: ConMed Corporation, Utica, NY (US)

(72) Inventors: Yuri Kazakevich, Newton, MA (US); Douglas D. Sjostrom, Tewksbury, MA (US)

(73) Assignee: ConMed Corporation, Utica, NY (US)

( * ) Notice: Subject to any disclaimer, the term of this patent is extended or adjusted under 35 U.S.C. 154(b) by 131 days.

(21) Appl. No.: 13/860,328

(22) Filed: Apr. 10, 2013

(65) Prior Publication Data

US 2013/0310648 A1      Nov. 21, 2013

Related U.S. Application Data

(60) Provisional application No. 61/622,368, filed on Apr. 10, 2012.

(51) Int. Cl.
*A61B 1/00*      (2006.01)
*G02B 23/24*    (2006.01)

(52) U.S. Cl.
CPC ......... *A61B 1/00193* (2013.01); *A61B 1/00066* (2013.01); *A61B 1/00179* (2013.01); *A61B 1/00183* (2013.01); *G02B 23/2415* (2013.01); *G02B 23/2476* (2013.01)

(58) Field of Classification Search
CPC ........... A61B 1/00193; A61B 1/00183; A61B 1/00179; G02B 23/2415; G02B 27/2228; G02B 27/2242

USPC ..................... 600/111, 166; 348/45
See application file for complete search history.

(56) References Cited

U.S. PATENT DOCUMENTS

| | | | |
|---|---|---|---|
| 5,133,035 A * | 7/1992 | Hicks ............................ | 385/117 |
| 5,459,605 A * | 10/1995 | Kempf ........................... | 359/462 |
| 5,689,365 A * | 11/1997 | Takahashi ..................... | 359/362 |
| 5,743,846 A * | 4/1998 | Takahashi et al. ............ | 600/166 |
| 2002/0022767 A1* | 2/2002 | Dohi et al. .................... | 600/173 |
| 2003/0083551 A1* | 5/2003 | Takahashi ..................... | 600/166 |
| 2005/0234345 A1* | 10/2005 | Yang ............................. | 600/476 |
| 2008/0027279 A1 | 1/2008 | Abou El Kheir | |
| 2008/0065104 A1 | 3/2008 | Larkin et al. | |
| 2012/0046679 A1 | 2/2012 | Patel et al. | |
| 2013/0030250 A1* | 1/2013 | Findeisen et al. ............ | 600/165 |
| 2013/0162776 A1* | 6/2013 | Noack ............................ | 348/45 |

FOREIGN PATENT DOCUMENTS

WO     WO2012041446     *  4/2012

* cited by examiner

*Primary Examiner* — John P Leubecker
(74) *Attorney, Agent, or Firm* — Pandiscio & Pandiscio

(57) ABSTRACT

A panning stereo endoscope which maintains an up-down orientation as the stereo endoscope pans an operative field, the panning stereo endoscope including a shaft having an axis; first and second optical channels extending along the shaft, each of the first and second optical channels having an off-axis direction of view; and an actuating mechanism carried by the shaft and adapted to (i) synchronously rotate the first and second optical channels about their respective axes, and (ii) synchronously, inversely piston the first and second optical channels along their respective axes.

14 Claims, 7 Drawing Sheets

360 DEGREE PANNING STEREO ENDOSCOPE

REFERENCE TO PENDING PRIOR PATENT APPLICATION

This patent application claims benefit of prior U.S. Provisional Patent Application Ser. No. 61/622,368, filed May 10, 2012 by Yuri Kazakevich et al. for 360 DEGREE PANNING STEREO ENDOSCOPE, which patent application is hereby incorporated herein by reference.

FIELD OF THE INVENTION

This invention relates to visualization systems in general, and more particularly to stereoscopic rigid endoscopes.

BACKGROUND OF THE INVENTION

Typically non-stereoscopic rigid endoscopes feature a single optical path extending from the distal end of the endoscope to the proximal end of the endoscope. The optical system typically includes, from distal end to proximal end, (i) an objective lens, (ii) one or more optical relays, and (iii) an ocular portion. The optical system defines the field of view of the endoscope, which typically ranges from about 60° to about 120°, depending on the types of medical procedures that the endoscope is designed to be used for.

In many circumstances this "instantaneous" field of view is too limited to allow the full operative field to be simultaneously viewed during the medical procedure. As a result, in order to expand the useful field of view, many commercially available endoscopes are designed to have an off-axis direction of view. This off-axis direction of view is achieved by providing a direction-of-view prism in the objective lens portion of the optical system. Typically endoscopes have 30, 45 or 70 degree direction-of-view angles as measured between the direction-of-view axis and the longitudinal axis of the endoscope shaft. Such endoscopes are offered by Karl Storz, Inc., Stryker, Inc., Olympus, Inc. and other manufacturers.

With an off-axis direction of view endoscope, the user can rotate the endoscope about the longitudinal axis of its shaft and effectively expand the "instantaneous" field of view by twice the angle of view value while the endoscope rotates (or "pans") about a full 360 degrees.

In the case of non-stereoscopic endoscopes, the endoscope is typically rotatably coupled to a video camera. In this situation, in order to expand the "instantaneous" field of view, the user simply axially rotates the endoscope relative to the coupled video camera, which is maintained in a relative "up and down" fixed orientation.

However, with rigid stereoscopic endoscopes, there are typically two parallel optical paths transferring independent optical images to a 3D video camera, where the separate images are received by image sensor(s), converted to electrical signals and further processed in order to be displayed on a 3D viewing device, e.g., a 3D monitor, a 3D head-mounted display or the like.

Due to the stereoscopic requirement for two separate optical paths, it is not possible to simply axially rotate the stereo endoscope relative to the stereo video camera. Thus, for the user to look right, left, up or down, the entire combination of camera and endoscope rotates, causing the displayed image to also rotate, in much the same manner as if one held a photograph in their hands and rotated the entire image. This situation causes significant inconvenience for the physician performing the endoscopic procedure since it becomes difficult to maintain an up-down orientation and goes against common practice developed over the years for non-stereoscopic endoscopy.

Thus there is a need for a new 360 degree panning stereo endoscope which maintains an up-down orientation as the stereo endoscope pans an operative field.

SUMMARY OF THE INVENTION

The present invention comprises the provision and use of a new 360 degree panning stereo endoscope which maintains an up-down orientation as the stereo endoscope pans an operative field.

In one preferred form of the invention, there is provided a panning stereo endoscope which maintains an up-down orientation as the stereo endoscope pans an operative field, the panning stereo endoscope comprising:
    a shaft having an axis;
    first and second optical channels extending along the shaft, each of the first and second optical channels having an off-axis direction of view; and
    an actuating mechanism carried by the shaft and adapted to (i) synchronously rotate the first and second optical channels about their respective axes, and (ii) synchronously, inversely piston the first and second optical channels along their respective axes.

In another preferred form of the invention, there is provided a method for stereoscopically viewing an operative field, the method comprising:
    providing a panning stereo endoscope which maintains an up-down orientation as the stereo endoscope pans an operative field, the panning stereo endoscope comprising:
        a shaft having an axis;
        first and second optical channels extending along the shaft, each of the first and second optical channels having an off-axis direction of view; and
        an actuating mechanism carried by the shaft and adapted to (i) synchronously rotate the first and second optical channels about their respective axes, and (ii) synchronously, inversely piston the first and second optical channels along their respective axes;
    positioning the panning stereo endoscope adjacent to an operative field; and
    viewing the operative field through the panning stereo endoscope and actuating the actuating mechanism.

BRIEF DESCRIPTION OF THE DRAWINGS

These and other objects, features and advantages of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

The present invention comprises the provision and use of a new 360 degree panning stereo endoscope. More particularly, the present invention provides a novel stereo endoscope which allows the user to view up, down, left or right incrementally, in a 360 degree arc, without altering the up-down orientation of the transmitted 3 dimensional image which is being viewed, e.g., on a viewing device such as a 3D monitor, a 3D head-mounted display, etc.

Figure 1:
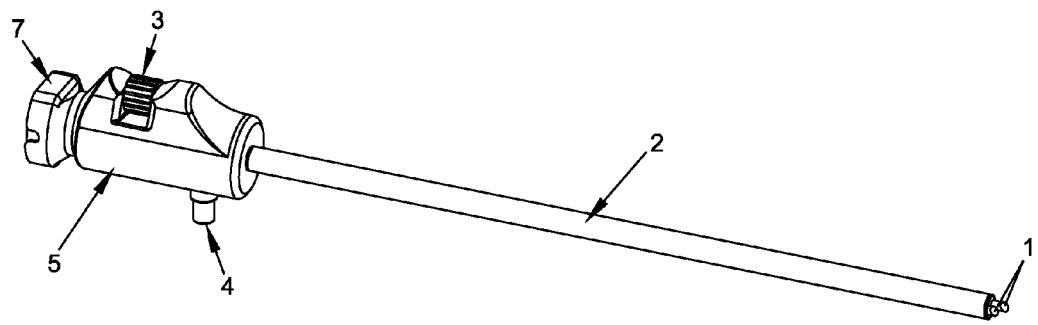
FIG. 1 is a schematic view of a novel 360 degree panning stereo endoscope formed in accordance with the present invention.

Looking first at FIG. 1, there is shown a stereoscopic endoscope 100 which comprises one preferred embodiment of the present invention. Stereoscopic endoscope 100 comprises two sets of identical moveable viewing optics 1 which protrude from the distal end of the shaft 2 of the stereo endoscope. These viewing optics 1 may be rotated, and advanced and retracted relative to one another, by rotating the knurled actuator 3 as will hereinafter be discussed in further detail. Also shown in FIG. 1 is the illumination fiber optic input adapter 4 which extends radially from the main body 5 of stereo endoscope 100.

Figure 1A:
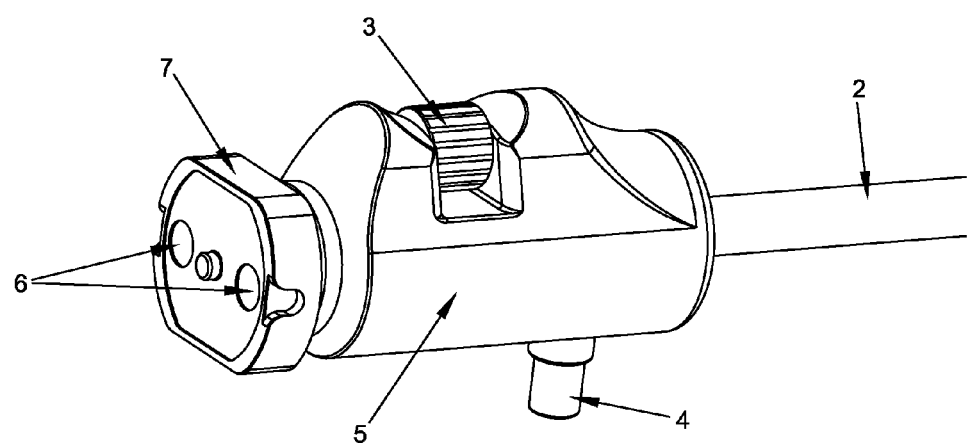
FIG. 1A is a schematic view showing further details of the proximal end of the stereo endoscope of FIG. 1.

Looking next at FIG. 1A, the two optical output windows 6 are shown on the proximal camera coupling interface 7 which is mounted to body 5 of stereo endoscope 100. Also shown in FIG. 1A is the knurled actuator 3. Rotating knurled actuator 3 causes the viewing optics 1 (which are preferably in the form of optics tube assemblies) to continuously rotate and piston through a 360 degree panning excursion. This 360 degree panning excursion may be clockwise or counterclockwise.

Figure 2A:
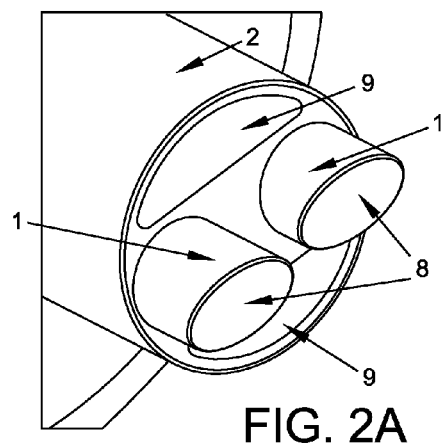
FIGS. 2A-2D are schematic views showing the distal end of the stereo endoscope of FIG. 1 in four different viewing positions.
Figure 2B:
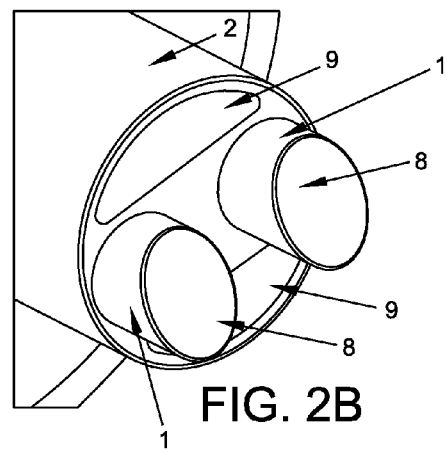
Figure 2C:
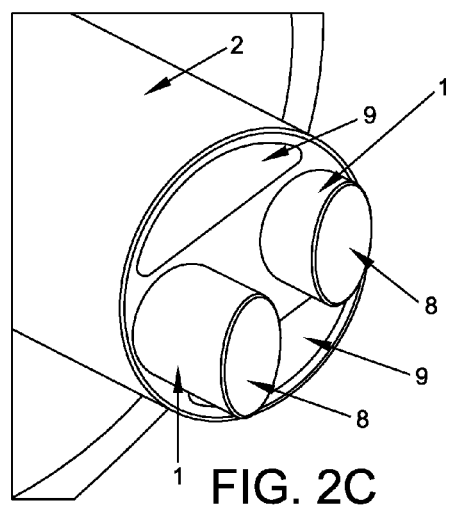
Figure 2D:
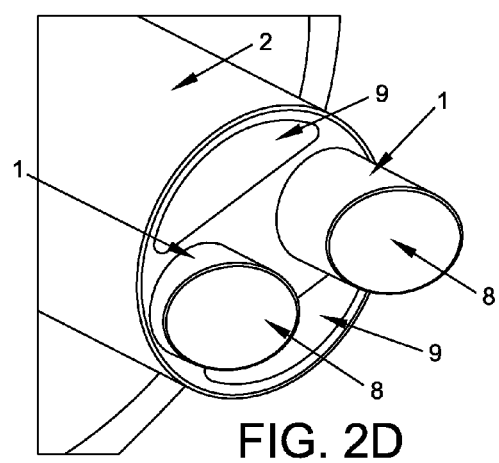

FIGS. 2A-2D show the distal end of stereoscopic endoscope 100 in four different viewing direction positions. More particularly, FIG. 2A shows the optics tube assemblies 1 in the "down" looking position. The field of view of each optics tube assembly 1 is approximately seventy degrees radiating from the oblique faces 8 of optics tube assemblies 1. Illuminating fiber optic bundles 9 are shown above and below optics tube assemblies 1. FIG. 2B shows optics tube assemblies 1 in the "up" looking position. Note how in FIG. 2B, oblique faces 8 of optics tube assemblies 1 have turned 180 degrees from the position shown in FIG. 2A. FIG. 2C shows optics tube assemblies 1 in the "left" looking position. Note how oblique faces 8 of optics tube assemblies 1 have rotated 90 degrees from the position shown in FIG. 2A. Note also how optics tube assemblies 1 have pistoned (i.e., one optics tube assembly 1 has moved forward and the other optics tube assembly 1 has moved rearward) from the position shown in FIG. 2A. FIG. 2D shows optics tube assemblies 1 in the "right" looking position. Note how the oblique faces 8 of optics tube assemblies 1 have rotated 90 degrees from the position shown in FIG. 2A. Note also how optics tube assemblies 1 have pistoned (i.e., one optics tube assembly 1 has moved rearward and the other optics tube assembly 1 has moved forward from the position shown in FIG. 2A.

Figure 3:
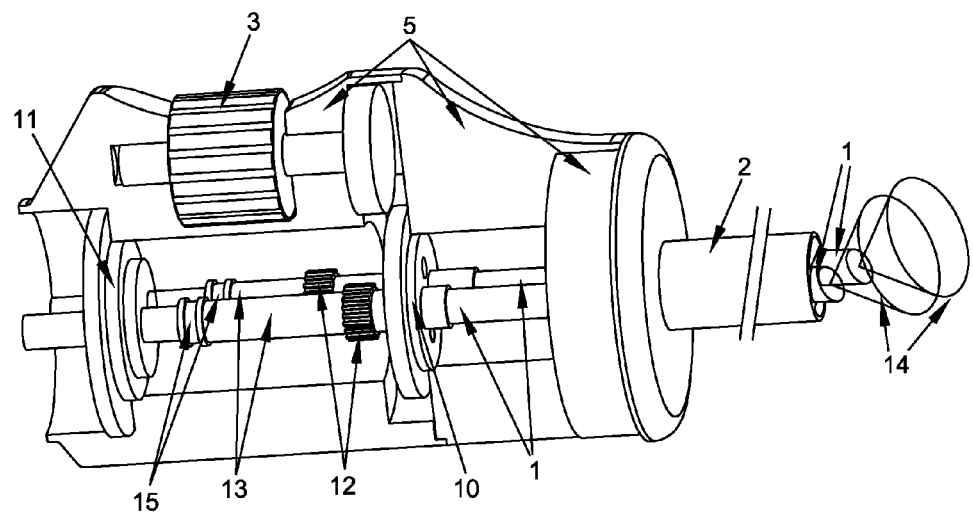
FIGS. 3-6, 7A-7C and 8 are schematic views showing details of the actuating mechanism of the stereo endoscope shown in FIG. 1.

FIG. 3 shows a shortened illustration of the distal end of stereo endoscope 100 and the innermost elements of the actuating mechanism contained within endoscope body 5 (which has been sectioned in this view). More particularly, two sets of identical optical elements are mounted within tubular elements so as to form the aforementioned optics tube assemblies 1, in a manner similar to that found in single channel rigid endoscopes. These two optics tube assemblies 1 are supported within endoscope body 5 by two alignment decks 10, 11. Two offset spur gears 12, which may be formed integral with, or mounted to, tubular sleeves 13, are fixed to the two optics tube assemblies 1, such that turning spur gears 12 causes optics tube assemblies 1 to turn. The angular positions of the two offset spur gears 12 are precisely matched during the assembly process, and fixed to optics tube assemblies 1 so as to establish and maintain the relationship of the two fields of view 14 provided by the two optics tube assemblies 1. As also seen in FIG. 3, two bearing sleeves 15, each featuring annular grooves, are also fixed to optics tube assemblies 1. Bearing sleeves 15 are fixed to optics tube assemblies 1 so as to be equidistant from the distal ends of the optics tube assemblies 1.

Figure 4:
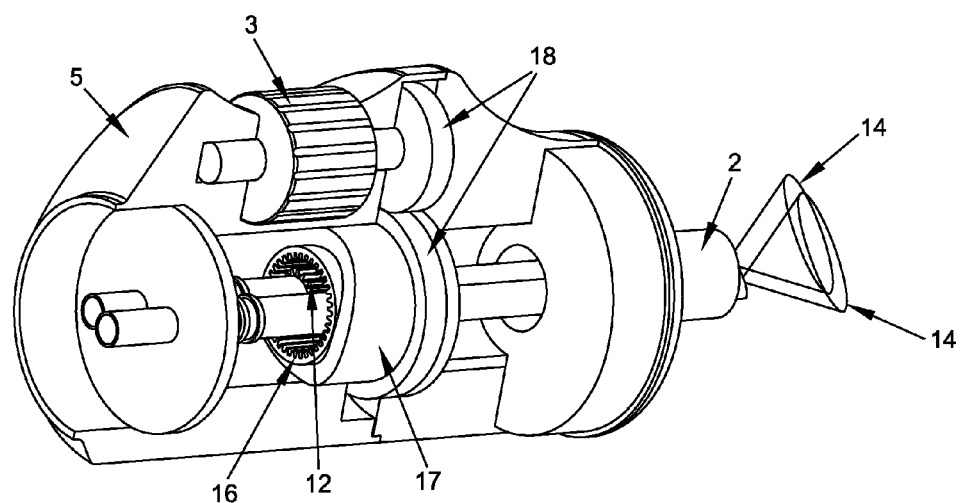

FIG. 4 shows further elements of the actuating mechanism contained within body 5 of stereoscopic endoscope 100. More particularly, the actuating elements contained within body 5 of stereo endoscope 100 comprise a ring gear 16 which engages the two spur gears 12. This gear train (i.e., the two spur gears 12 and ring gear 16) is designed to provide two revolutions of spur gears 12 to each revolution of ring gear 16. Ring gear 16 is secured to a face cam 17. Face cam 17 is contoured to provide one complete proximal-distal reciprocating excursion of optical tube assemblies 1 for each complete revolution of their respective spur gears 12 as will hereinafter be discussed. In addition, the timing of face cam 17 to the gear train (i.e., to the two spur gears 12 and ring gear 16) is such that when the view is "up" (FIG. 2B), or "down" (FIG. 2A), the timing of face cam 17 will be mid-excursion, and optics tube assemblies 1 will protrude an equal distance from the distal end of the endoscope, as will also hereinafter be discussed. Actuator 3 is captive and rotationally sealed within body 5 of stereo endoscope 100 with only its knurled outer surface protruding from the interior of body 5. Actuator 3, when revolved by the user, rotates the cam-ring gear assembly by way of a gear or timing belt connection 18. In this way, rotation of actuator 3 rotates face cam 17 and ring gear 16, whereby to rotate and piston optics tube assemblies 1 as will hereinafter be discussed.

Figure 5:
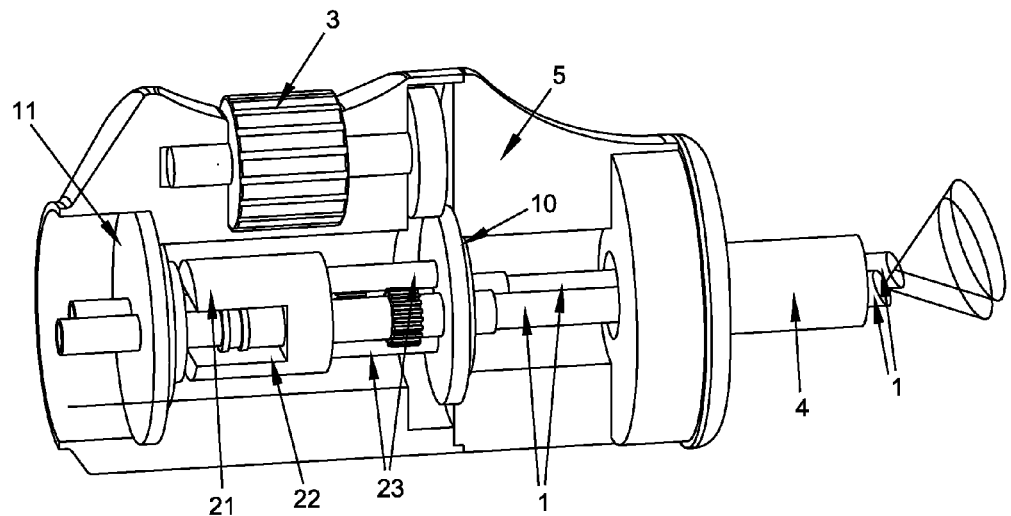
Figure 6:
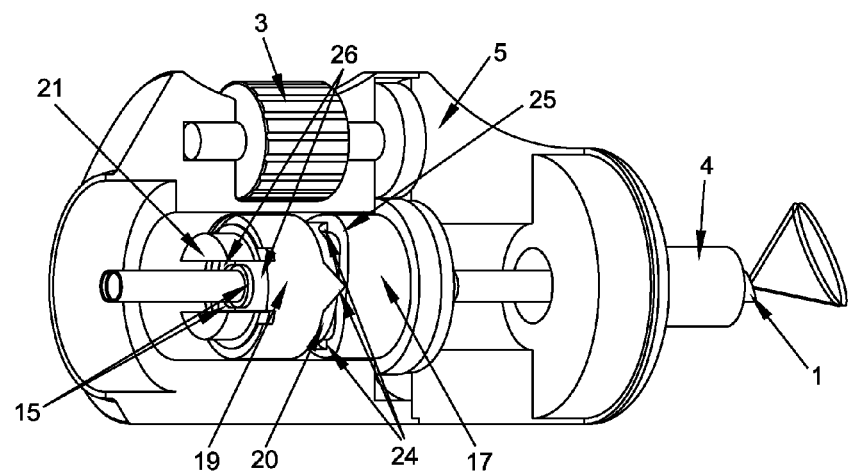

FIG. 5 shows the internal support and alignment elements for the face cam followers 19, 20 (which are themselves shown in FIG. 6). In FIG. 5, ring gear 16 and face cam 17 have been hidden for the sake of clarity. FIG. 5 shows the inner cam follower alignment and bearing component 21 which serves as an inner bearing for the inner cam follower 20 (FIG. 6). Inner cam follower alignment and bearing component 21 comprises a transverse slot 22 (FIG. 5) for holding the inner and outer cam follower elements 19, 20, respectively.

Inner cam follower alignment and bearing component 21 is maintained in position, with its transverse slot 22 appropriately oriented within housing 5, by two double-shouldered stanchion pins 23 (FIG. 5).

FIG. 6 shows inner face cam follower 20 and outer face cam follower 19 with their respective points 24 in position on the cam portion 25 of face cam 17. As may be seen in FIGS. 7A-7C, each cam follower 19, 20 has two follower points 24, with each follower point 24 being set 180 degrees from the other follower point 24 on a given cam follower. As may also be seen in FIGS. 7A-7C, the two follower points 24 of one cam follower are offset 90 degrees from the two follower points of the other cam follower. Inner and outer cam followers 19, 20 are configured such that their respective alignment tabs 26 (FIGS. 6 and 7) are restrained within the transverse slot 22 of inner cam follower alignment and bearing component 21 such that their respective pairs of follower points 24 are maintained 90 degrees from each other. As a result of the foregoing, when the lobes of cam portion 25 of face cam 17 are revolved one complete rotation, cam followers 19, 20 will each make two complete reciprocating movement cycles.

More particularly, when face cam 17 is revolved one complete revolution, cam followers 19, 20 will have been in the maximum distal position twice and the maximum proximal position twice, and each of cam followers 19, 20 will have been aligned, mid-cycle, in the median position twice.

The distal/proximal cam excursion limits correspond to the FIG. 2D ("right") or FIG. 2C ("left") viewing directions, respectively. The median position of cam followers 19, 20 corresponds to FIG. 2A ("down") or FIG. 2B ("up") viewing directions, respectively.

This reciprocal motion of face cam followers 19, 20, and hence optics tube assemblies 1, is desirable so that when looking in the "right" or "left" directions, the tip of one optics tube assembly 1 does not partially "eclipse" the field of view of the other optics tube assembly 1.

Figure 7A:
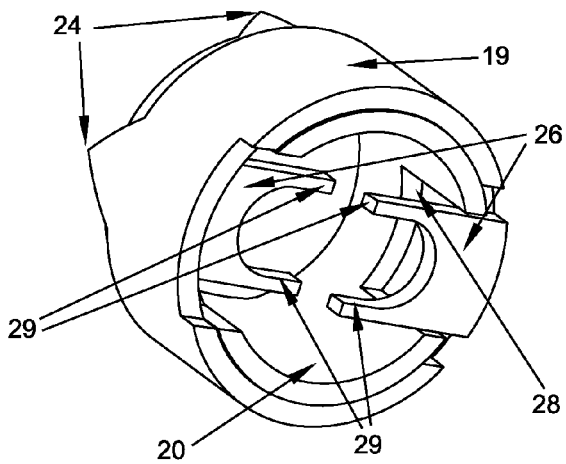
Figure 7B:
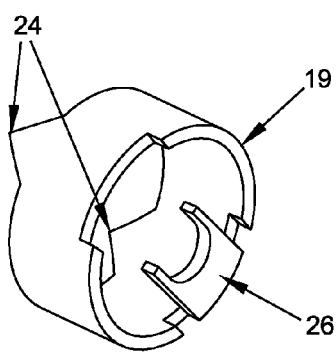
Figure 7C:
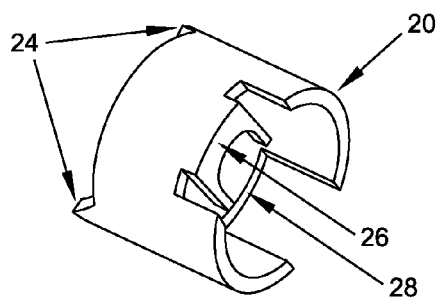

FIGS. 7A-7C show further details of inner cam follower 20 and outer cam follower 19. Each of the inner and outer cam followers 20, 19 features an alignment tab 26 which rides within the slot 22 of inner cam follower alignment and bearing component 21. In addition, alignment tab 26 of outer cam follower 19 rides in a slot 28 formed in inner cam follower 20. Alignment tabs 26 are each configured with two forks 29 which are designed to be captured within the corresponding grooves of bearing sleeves 15 of optics tube assemblies 1. FIGS. 7A-7C also show how each of the cam followers 19, 20 comprises a pair of follower points 24 which are disposed 180 degrees from each other.

Figure 8:
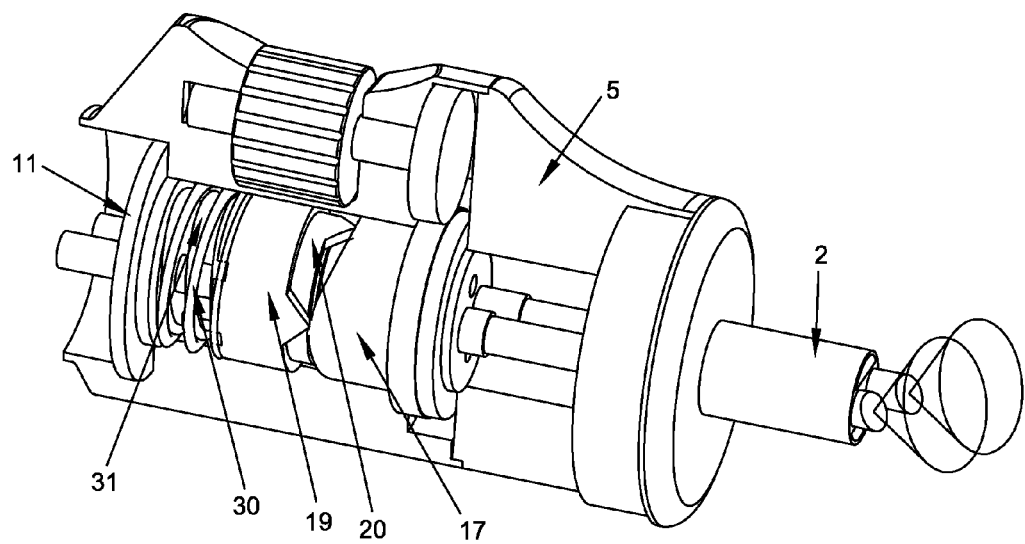

FIG. 8 shows the complete actuating (rotary/reciprocation) mechanism contained within endoscope body 5. FIG. 8 also shows two return springs 30, 31 which maintain cam followers 19, 20, respectively, in contact with the lobes of face cam 17. Springs 30, 31 are sized to match the outside and inside diameters of their respective cam followers 19, 20 with sufficient clearances so as not to bind with any surrounding elements during the operating cycle of the stereo endoscope. In addition, springs 30, 31 are wound counter to one another for the same reason, i.e., one is left-hand wound and the other is right-hand wound. Springs 30, 31 are constrained in proper compression by alignment deck 11 which is fastened to endoscope body 5.

On account of the foregoing, it will be appreciated that rotation of actuator 3 by the user causes gear or timing belt connection 18 to rotate face cam 17. Rotation of face cam 17 causes ring gear 16 to turn spur gears 12, which in turn causes optical tube assemblies 1 to rotate. At the same time, rotation of face cam 17 causes cam followers 19, 20 to move longitudinally, which in turn causes optics tube assemblies 1 to move longitudinally. Thus, rotation of actuator 3 causes optics tube assemblies 1 to simultaneously rotate and piston. Significantly, due to fact that points 24 on cam followers 19, 20 are offset at 90 degree intervals, optics tube assemblies 1 piston inversely relative to one another, i.e., as one optics tube assembly 1 pistons forward, the other optics tube assembly 1 pistons rearwardly. Thus it will be seen that rotation of actuator 3 by the user simultaneously causes optics tube assemblies 1 to both rotate and piston, with such positioning being in inverse relation, whereby to provide a 360 degree panning stereo endoscope.

FIGS. 1-8 show one preferred embodiment of the present invention, wherein stereo endoscope 100 detachably attaches to a 3D video camera via camera coupling interface 7. However, if desired, stereo endoscope 100 may be permanently coupled to, and integrated with, a 3D camera.

Furthermore, FIGS. 1-8 show a construction employing a manually-driven knurled actuator 3. Alternatively, the same actuation can be effected by a motorized rotation that can be controlled by a push button or slider switch disposed at the 3D camera, or on a floor pedal, etc.

Figure 9:
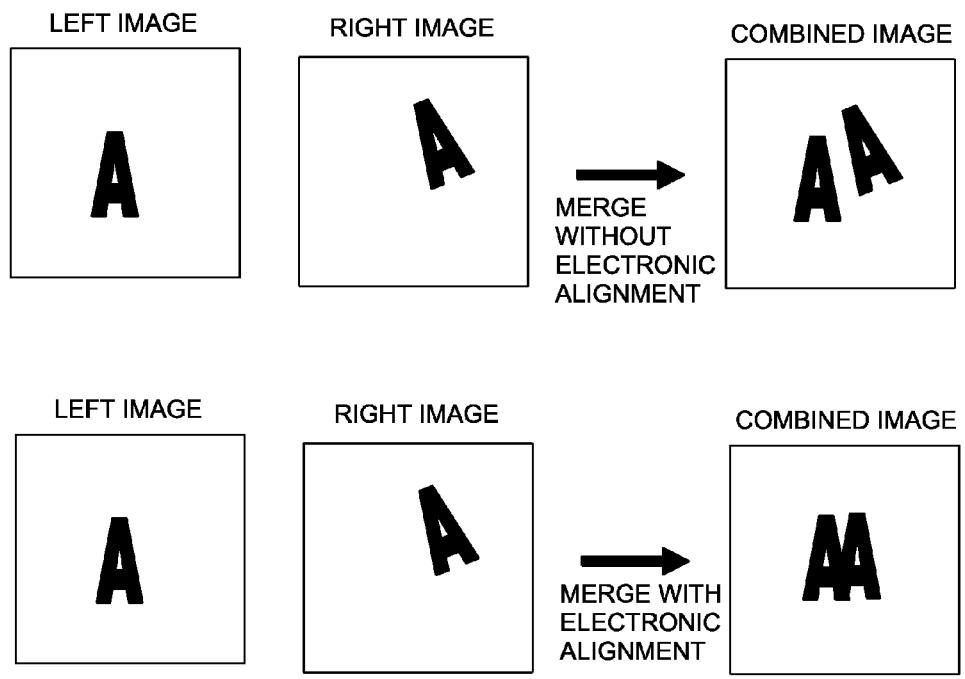
FIG. 9 is a schematic view showing an electronic alignment method which may be applied to the stereo endoscope shown in FIG. 1 (note that in FIG. 9, the degree of misalignment has been exaggerated somewhat for clarity of understanding).

In still another form of the invention, electronic alignment methods can be utilized. More particularly, in stereo endoscopy, the alignment between the right and left channel images is important. More particularly, with stereo endoscopy, the right and left channel images must be aligned vertically, horizontally and rotationally. Since the present invention comprises both rotational and axial movement of individual optical channels, keeping proper alignment by opto-mechanical means may be challenging. One way to alleviate this issue is to apply an electronic alignment method. More particularly, such an electronic alignment method may utilize an alignment algorithm which includes the comparison of left and right images (or parts of the left and right images) of a live scene captured by the 3D camera. The left and right images are evaluated for misalignment, and then electronically brought into alignment by image processing means. See FIG. 9 (note that in FIG. 9, the degree of misalignment has been exaggerated somewhat for clarity of understanding). In this respect it should be appreciated that image processing for electronic alignment does not need to be enabled at all times during the medical procedure, which could be too computer intensive and impractical. Rather, inasmuch as misalignment is most likely to result from the panning action, the electronic alignment can be electronically coupled to the actuation mechanism and then enabled for an alignment cycle only after the user changes the direction of view of the stereo endoscope (i.e., by actuating knurled actuator 3).

MODIFICATIONS

While the present invention has been described in terms of certain exemplary preferred embodiments, it will be readily understood and appreciated by those skilled in the art that it is not so limited, and that many additions, deletions and modifications may be made to the preferred embodiments discussed herein without departing from the scope of the present invention.

What is claimed is:

1. A panning stereo endoscope which maintains an up-down orientation as the stereo endoscope pans an operative field, the panning stereo endoscope comprising:
    a shaft having an axis;
    first and second optical channels extending along the shaft, each of the first and second optical channels having an off-axis direction of view; and
    an actuating mechanism carried by the shaft and adapted to (i) synchronously rotate the first and second optical channels about their respective axes, and (ii) synchronously, inversely piston the first and second optical channels along their respective axes;
    wherein each of the first and second optical channels comprises a direction of view prism, an objective lens, at least one optical relay and an ocular portion;
    wherein the direction of view prism, the objective lens, the at least one optical relay and the ocular portion together comprise an optics tube assembly configured to rotate and piston as a unit; and
    wherein the actuating mechanism comprises a ring gear and a cam, the ring gear and the cam being connected so that they rotate in unison.

2. A panning stereo endoscope according to claim 1 wherein the ring gear turns first and second spur gears mounted to the first and second optics tube assemblies so as to synchronously rotate the first and second optics tube assemblies about their respective axes.

3. A panning stereo endoscope according to claim 1 further comprising first and second cam followers mounted to the first and second optics tube assemblies, respectively, the first and second cam followers riding on the cam so as to synchronously, inversely piston the first and second optical channels along their respective axes.

4. A panning stereo endoscope according to claim 3 wherein the cam comprises a cam face having two distally-positioned portions and two proximally-positioned portions, wherein the two distally-positioned portions are diametrically opposed to one another and the two proximally-positioned portions are diametrically opposed to one another.

5. A panning stereo endoscope according to claim 4 wherein the first and second cam followers each comprise two follower points for riding on the cam face, and further wherein the two follower points are diametrically opposed to one another.

6. A panning stereo endoscope according to claim 5 wherein the first and second cam followers are offset from one another by 90 degrees.

7. A panning stereo endoscope according to claim 1 further comprising means for rotating the ring gear and the cam.

8. A method for stereoscopically viewing an operative field, the method comprising:
  providing a panning stereo endoscope which maintains an up-down orientation as the stereo endoscope pans an operative field, the panning stereo endoscope comprising:
    a shaft having an axis;
    first and second optical channels extending along the shaft, each of the first and second optical channels having an off-axis direction of view; and
    an actuating mechanism carried by the shaft and adapted to (i) synchronously rotate the first and second optical channels about their respective axes, and (ii) synchronously, inversely piston the first and second optical channels along their respective axes;
    wherein each of the first and second optical channels comprises a direction of view prism, an objective lens, at least one optical relay and an ocular portion;
    wherein the direction of view prism, the objective lens, the at least one optical relay and the ocular portion together comprise an optics tube assembly configured to rotate and piston as a unit;
    wherein the actuating mechanism comprises a ring gear and a cam, the ring gear and the cam being connected so that they rotate in unison;
  positioning the panning stereo endoscope adjacent to an operative field; and
  viewing the operative field through the panning stereo endoscope and actuating the actuating mechanism.

9. A method according to claim 8 wherein the ring gear turns first and second spur gears mounted to the first and second optics tube assemblies so as to synchronously rotate the first and second optics tube assemblies about their respective axes.

10. A method according to claim 8 further comprising first and second cam followers mounted to the first and second optics tube assemblies, respectively, the first and second cam followers riding on the cam so as to synchronously, inversely piston the first and second optical channels along their respective axes.

11. A method according to claim 10 wherein the cam comprises a cam face having two distally-positioned portions and two proximally-positioned portions, wherein the two distally-positioned portions are diametrically opposed to one another and the two proximally-positioned portions are diametrically opposed to one another.

12. A method according to claim 11 wherein the first and second cam followers each comprise two follower points for riding on the cam face, and further wherein the two follower points are diametrically opposed to one another.

13. A method according to claim 12 wherein the first and second cam followers are offset from one another by 90 degrees.

14. A method according to claim 8 further comprising means for rotating the ring gear and the cam.

\* \* \* \* \*